(12) United States Patent
Berg et al.

(10) Patent No.: US 6,416,527 B1
(45) Date of Patent: *Jul. 9, 2002

(54) VESSEL CUTTING DEVICE

(75) Inventors: Todd Allen Berg, Lino Lakes; Christopher M. Prigge, New Hope, both of MN (US)

(73) Assignee: St. Jude Medical Cardiovascular Group, Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 226 days.

(21) Appl. No.: 09/014,759

(22) Filed: Jan. 28, 1998

(51) Int. Cl.⁷ .............................................. A61B 17/32
(52) U.S. Cl. ...................................... 606/180; 606/184
(58) Field of Search .............................. 606/184, 159, 606/180, 191

(56) References Cited

U.S. PATENT DOCUMENTS

| 5,488,958 A | * | 2/1996 | Topel et al. ............ 606/184 X |
| 5,676,670 A | | 10/1997 | Kim ............................. 606/108 |
| 5,702,412 A | | 12/1997 | Popov et al. ................ 606/159 |
| 5,830,222 A | * | 11/1998 | Makower .................... 606/159 |

FOREIGN PATENT DOCUMENTS

| EP | 0 807 412 A1 | 11/1997 | ........... A61B/17/32 |
| WO | WO 97/13463 A | 4/1997 | ........... A61B/17/00 |

* cited by examiner

Primary Examiner—Michael H. Thaler
(74) Attorney, Agent, or Firm—Fish & Neave; Robert R. Jackson

(57) ABSTRACT

A catheter-based system for accessing specific body cavities percutaneously and minimizing patient trauma is provided. In the preferred embodiment, in order to create an aperture at an access site in a patient's existing tubular body organ structure, a delivery sheath is passed axially along the interior of a portion of the existing tubular body organ structure to place a distal end of the delivery sheath near the access site. A centering wire is passed axially along the interior of the delivery sheath, piercing through from inside to outside of the patient's existing tubular body organ structure at the access site by causing an end portion of the centering wire to emerge from the distal end of the delivery sheath. A cutting catheter is passed substantially coaxially over the centering wire and axially along the interior of the delivery sheath. The aperture is formed by advancing a distal end of the cutting catheter through from inside to outside of the patient's existing tubular body organ structure at the access site and advancing the distal end of the delivery sheath through from inside to outside of the patient's existing tubular body organ structure at the access site.

26 Claims, 5 Drawing Sheets

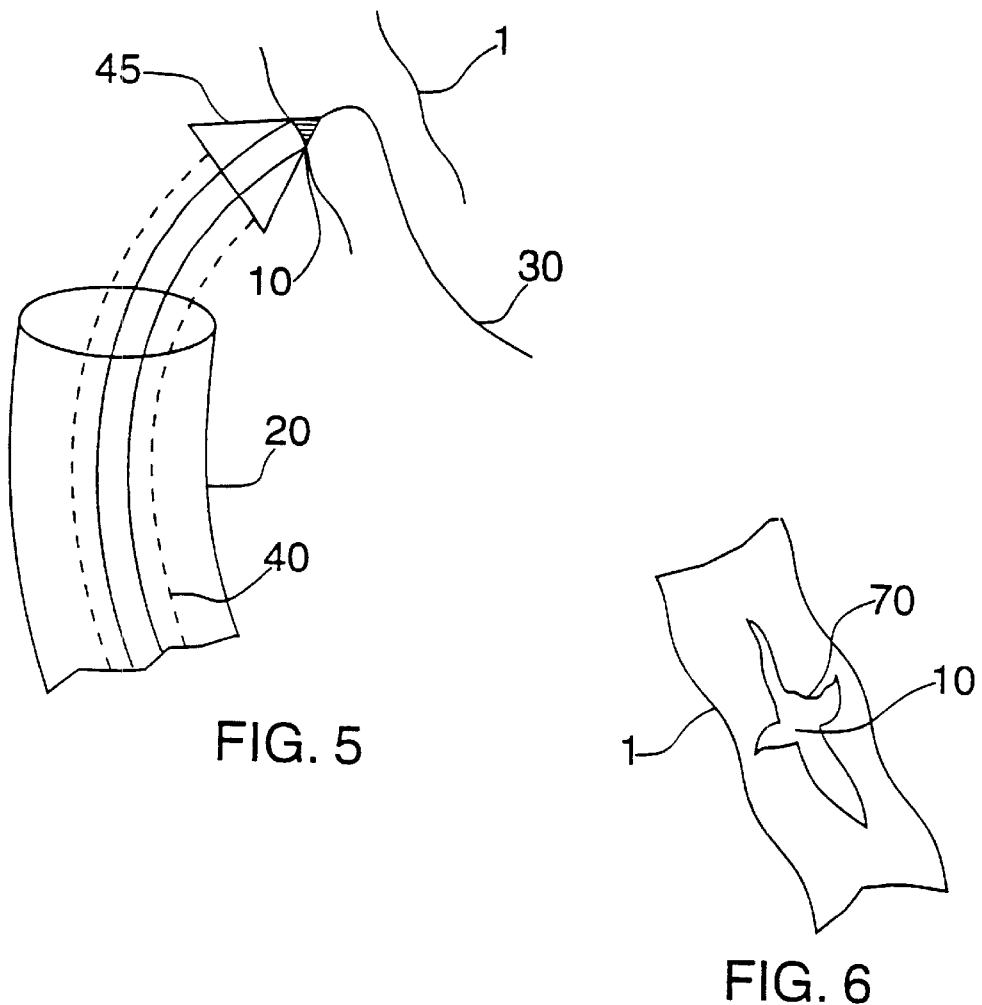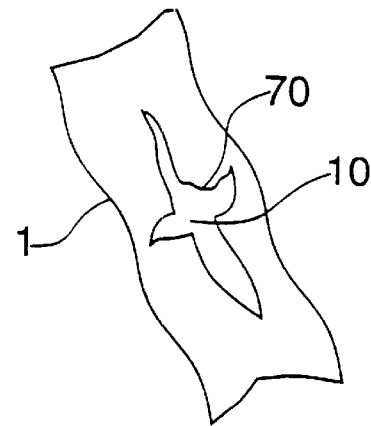
FIG. 5
FIG. 6
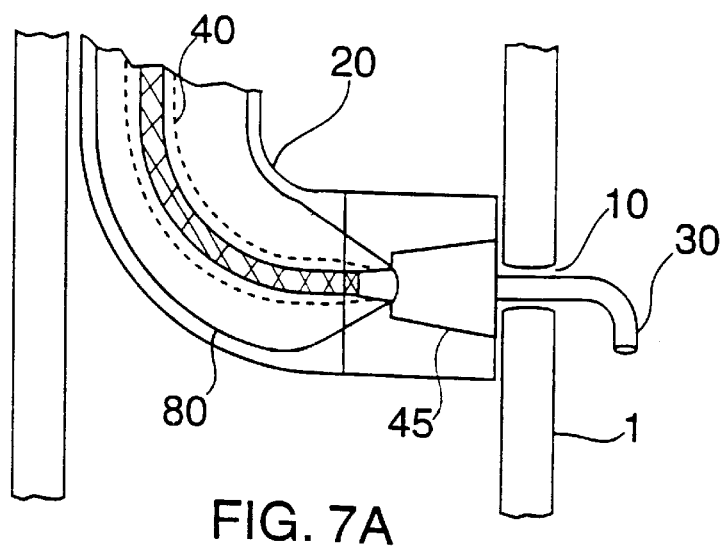
FIG. 7A

VESSEL CUTTING DEVICE

BACKGROUND OF THE INVENTION

This invention relates to vessel cutting devices for use in the repair, replacement or supplement of a medical patient's natural body organ structures or tissues. More particularly, this invention relates to vessel cutting devices for use in vascular anastomosis (the surgical connection of vessels).

An example of the possible uses of the invention is a minimally invasive cardiac bypass procedure. This and other examples are considered in detail in Goldsteen et al., U.S. patent application Ser. No. 08/745,618, filed Nov. 7, 1996, which is hereby incorporated by reference herein in its entirety.

Vascular anastomosis is a delicate and time-consuming procedure in which fast and accurate vessel cutting plays a particularly important role.

In view of the foregoing, it would be desirable to provide a catheter-based system for accessing specific body cavities percutaneously, thereby minimizing patient trauma.

It would also be desirable to provide fast and accurate vessel cutting devices.

SUMMARY OF THE INVENTION

It is an object of the present invention to provide a catheter-based system for accessing specific body cavities percutaneously, thereby minimizing patient trauma. It is also an object to provide fast and accurate vessel cutting devices.

These and other objects are accomplished by providing a method and apparatus for creating an aperture at an access site in a patient's existing tubular body organ structure by passing a delivery sheath axially along the interior of a portion of the existing tubular body organ structure to place a distal end of the delivery sheath near the access site, passing a centering wire axially along the interior of the delivery sheath, piercing through from inside to outside of the patient's existing tubular body organ structure at the access site by causing an end portion of the centering wire to emerge from the distal end of the delivery sheath, passing a cutting catheter substantially coaxially over the centering wire and axially along the interior of the delivery sheath, forming the aperture by advancing a distal end of the cutting catheter through from inside to outside of the patient's existing tubular body organ structure at the access site and advancing the distal end of the delivery sheath through from inside to outside of the patient's existing tubular body organ structure at the access site.

In one embodiment, the distal end of the cutting catheter is rotated to cut through the patient's existing tubular body organ structure at the access site. In another embodiment, a cutting catheter with a conical (preferably star-shaped) cutting edge is pushed through the patient's existing tubular body organ structure at the access site.

The present invention can also be used to create an aperture in the patient's existing tubular body organ structure by advancing a distal end of the cutting catheter through from outside to inside of the patient's existing tubular body organ structure at the access site.

In the most preferred embodiment, all or substantially all necessary apparatus is inserted into the patient via the patient's existing body organ vessel. In addition, all or substantially all apparatus functions are controlled by the physician (a term used herein to also include supporting technicians) from outside the patient's body.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIG. 5 is a simplified elevational view, partly in section, showing the distal end of the cutting catheter advancing through from outside to inside to create an aperture in the patient's existing tubular body organ structure;

FIG. 6 is a side view of the patient's existing tubular body organ structure of FIG. 5, showing the aperture created;

FIG. 7a is still another view similar to FIG. 1a showing the distal end of a delivery sheath in the interior of a portion of the existing tubular body organ structure with a centering wire piercing through from inside to outside of the patient's existing tubular body organ structure at the access site, wherein the cutting catheter includes a dilator;

DETAILED DESCRIPTION OF THE INVENTION

Figure 1A:
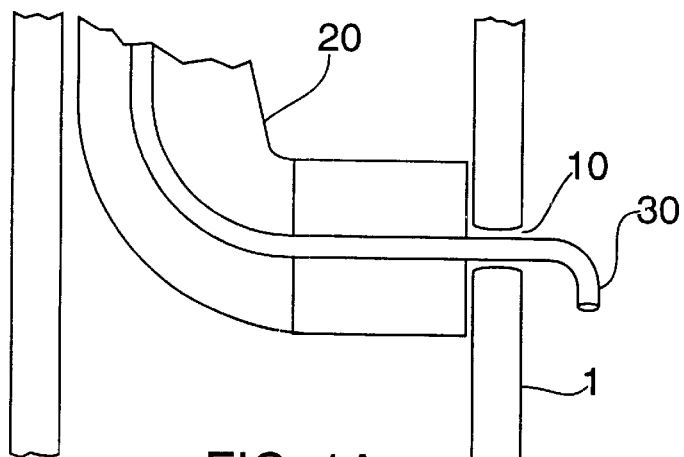
FIG. 1a is a simplified sectional view showing the distal end of a delivery sheath in the interior of a portion of the existing tubular body organ structure with a centering wire piercing through from inside to outside of the patient's existing tubular body organ structure at the access site.

As a preliminary step in creating an aperture at an access site 10 in a patient's existing tubular body organ structure 1, a delivery sheath 20 is passed axially along the interior of a portion of tubular body organ structure 1 to place a distal end of delivery sheath 20 near access site 10. When the distal end of delivery sheath 20 is adjacent to access site 10, a centering wire 30 is passed axially along the interior of the sheath until the end portion of centering wire 30 emerges from the distal end of the sheath and pokes through from inside to outside of tubular body organ structure 1. Centering wire 30 provides a pilot track for cutting catheter 40 to follow. FIG. 1*a* shows the distal end of delivery sheath 20 in the interior of a portion of tubular body organ structure 1 with a centering wire 30 piercing through from inside to outside of the organ structure at access site 10.

Figure 1B:
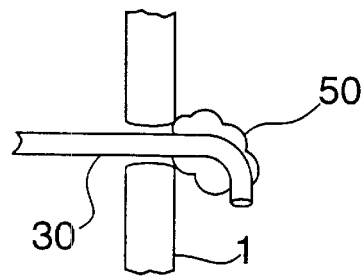
FIG. 1b is a view similar to portions of FIG. 1a showing a centering wire piercing through from inside to outside of the patient's existing tubular body organ structure at the access site, wherein the end portion of the centering wire includes a selectively enlargeable structure.
Figure 1C:
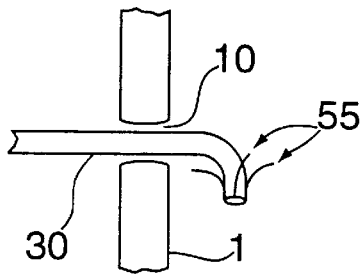
FIG. 1c is another view similar to portions of FIG. 1a showing a centering wire piercing through from inside to outside of the patient's existing tubular body organ structure at the access site, wherein the end portion of the centering wire includes fasteners.

The distal end of centering wire 30 is preferably deformable to facilitate deployment and removal, but resumes its operational (preferably hooked) shape once deployed. Centering wire 30 is kept relatively straight when it is inside sheath 20. But, when centering wire 30 is pushed axially out the distal end of sheath 20, it curves to one side, as shown in FIGS. 1*a*, 1*b* and 1*c*. FIGS. 1*b* and 1*c* show alternative structures for centering wire 30. In FIG. 1*b*, the end portion of centering wire 30 includes a selectively enlargeable structure (such as a balloon 50 which extends annularly around the exterior of the centering wire and projects radially outwardly from the centering wire in all radially outward directions when inflated). In FIG. 1*c*, the end portion of centering wire 30 includes struts 55 spaced circumferentially around centering wire 30 and which are resiliently biased to project from the centering wire after the end portion of the centering wire pierces through body organ structure 1 at access site 10. By providing a selectively enlargeable structure disposed on the exterior of the centering wire at a predetermined distance proximally from the distal end of the centering wire and enlarging that structure after the centering wire has pierced organ structure 1, it is possible to prevent the portion of centering wire 30 which is distal of the enlargeable structure from passing back into the organ structure. In addition to the retaining function, the enlargeable structure serves to seal the aperture and displace tissue from around the outside of organ structure 1 near access site 10, thereby creating a space. Such a space helps to prevent cutting head 45 from cutting other tissues after exiting organ structure 1 at access site 10.

Figure 2:
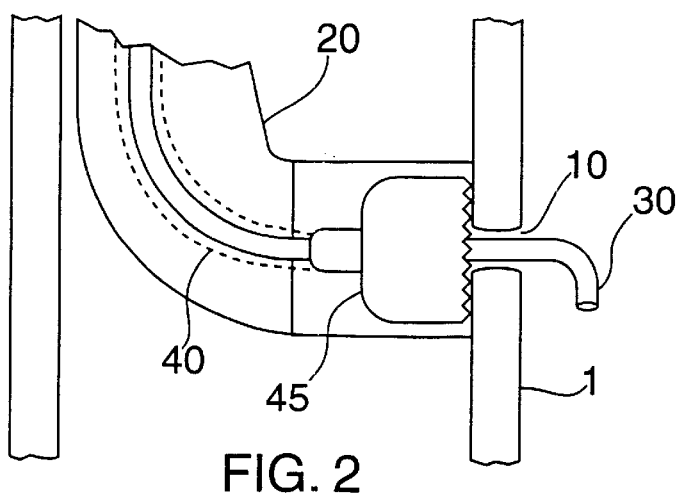
FIG. 2 is yet another view similar to FIG. 1a showing a cutting catheter positioned for cutting at the distal end of a delivery sheath at the access site.

After piercing through organ structure 1 at access site 10 with centering wire 30, cutting catheter 40 is passed substantially coaxially over the centering wire and axially along the interior of sheath 20. FIG. 2 shows cutting head 45 of cutting catheter 40 positioned for cutting at the distal end of delivery sheath 20 at access site 10.

Figure 3:
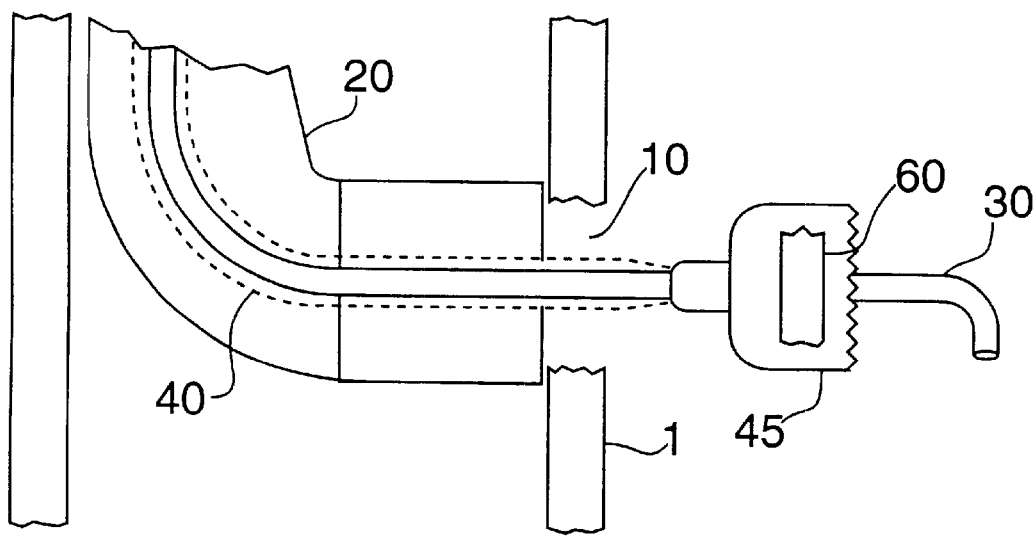
FIG. 3 is still another view similar to FIG. 1a showing forming the aperture by advancing a distal end of the cutting catheter through from inside to outside of the patient's existing tubular body organ structure at the access site.

Centering wire 30 holds cutting catheter 40 and delivery sheath 20 against organ structure 1 at access site 10, thereby preventing undue bleeding during and after the creation of the aperture that could occur if the cutting catheter and the delivery sheath were to move away from the access site. FIG. 3 shows how the aperture is formed by advancing the distal end of cutting catheter 40 (i.e., cutting head 45) through from inside to outside of organ structure 1 at access site 10 by rotating and/or pushing the distal end of the cutting catheter.

Figure 4:
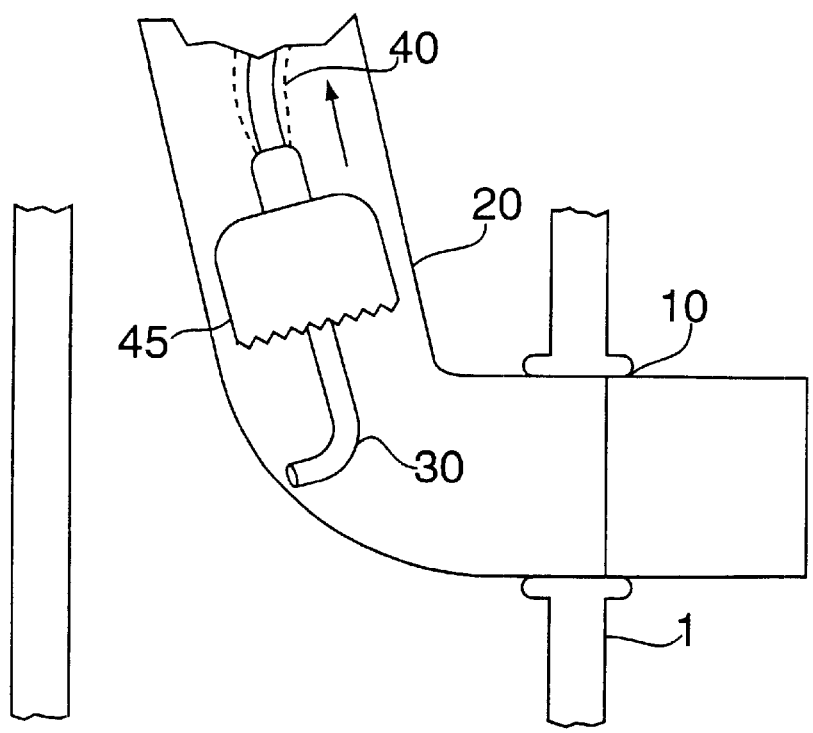
FIG. 4 is yet another view similar to FIG. 1a showing advancing the distal end of the delivery sheath through from inside to outside of the patient's existing tubular body organ structure at the access site.

As shown in FIGS. 2, 3, and 4, the distal end of cutting catheter 40 has a circular cutting edge. Cutting catheter 40, which when advanced by rotation, cuts through tissue and removes tissue plug 60. The preferred embodiment of cutting head 45 also includes a serrated cutting edge and an axially aligned recess for accepting tissue plug 60. By removing plug 60 of tissue (rather than merely displacing tissue, as in FIGS. 5 and 6), the elastic recoil of organ structure 1 at access site 10 is reduced, which may be a desirable condition for optimal graft attachment.

FIG. 4 shows advancing the distal end of delivery sheath 20 through from inside to outside of organ structure 1 at access site 10 and removing centering wire 30 and cutting catheter 40 along with tissue plug 60 contained within cutting head 45.

As shown in FIG. 5, non-rotating cutting catheter 40 can be used to create specific geometric aperture shapes (e.g., oblong aperture 70 for coronary anastomosis). FIG. 5 also shows the use of the present invention in creating an aperture in organ structure 1 by advancing a distal end of cutting catheter 40 through from outside to inside of the organ structure at access site 10. Centering wire 30 is tracked through cutting catheter 40 and is shown piercing organ structure 1 at access site 10. Following such an outside-to-inside aperture, delivery sheath 20 can be passed axially along the interior of a portion of organ structure 1 to place a distal end of delivery sheath 20 near second access site 10 where an inside-to-outside aperture can be created. (Note that organ structure 1 is shown smaller in scale relative to sheath 20 and cutting catheter 40.)

FIG. 6 is a side view of organ structure 1, showing aperture 70 created using non-rotating cutting catheter 40 of FIG. 5.

Figure 7B:
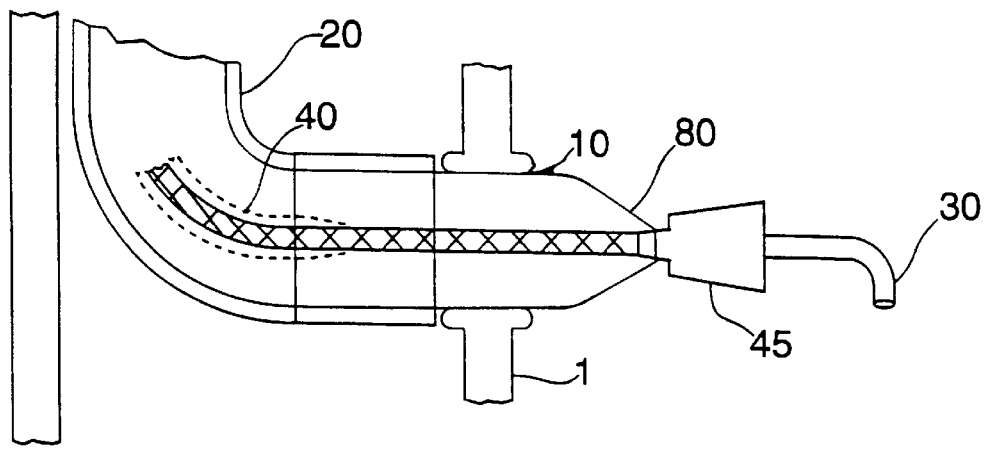
FIG. 7b is yet another view similar to FIG. 1a forming the aperture by advancing a distal end of the cutting catheter through from inside to outside of the patient's existing tubular body organ structure at the access site, wherein the cutting catheter includes a dilator.
Figure 7C:
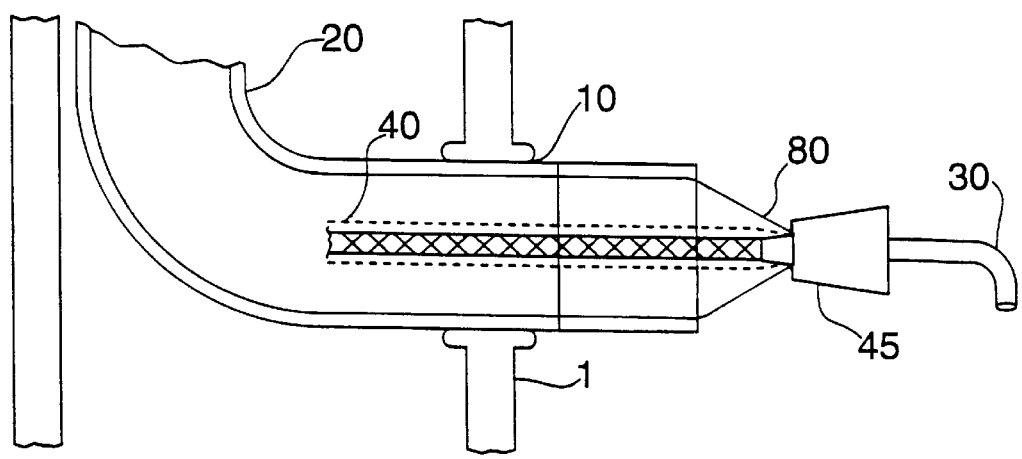
FIG. 7c is still another view similar to FIG. 1a showing advancing the delivery sheath through the aperture at the access site.

Cutting catheter 40 shown in FIG. 7*a* is a rotating catheter. Cutting head 45 could be a saw-tooth or a razor-edge type, for example. The distal end of delivery sheath 20 is shown in the interior of a portion of organ structure 1 with centering wire 30 piercing through from inside to outside of the organ structure at access site 10, wherein cutting catheter 40 includes dilator 80. Dilator 80 facilitates advancing sheath 20 through the aperture (as is shown by the succession of steps illustrated by FIGS. 7*b* and 7*c*).

The outer diameter of dilator 80 is close to the inner diameter of sheath 20 and is typically larger than the diameter of cutting head 45. As shown in FIG. 7*b*, as dilator 80 advances through the aperture at access site 10, the aperture is simultaneously sealed against bleeding.

Figure 8:
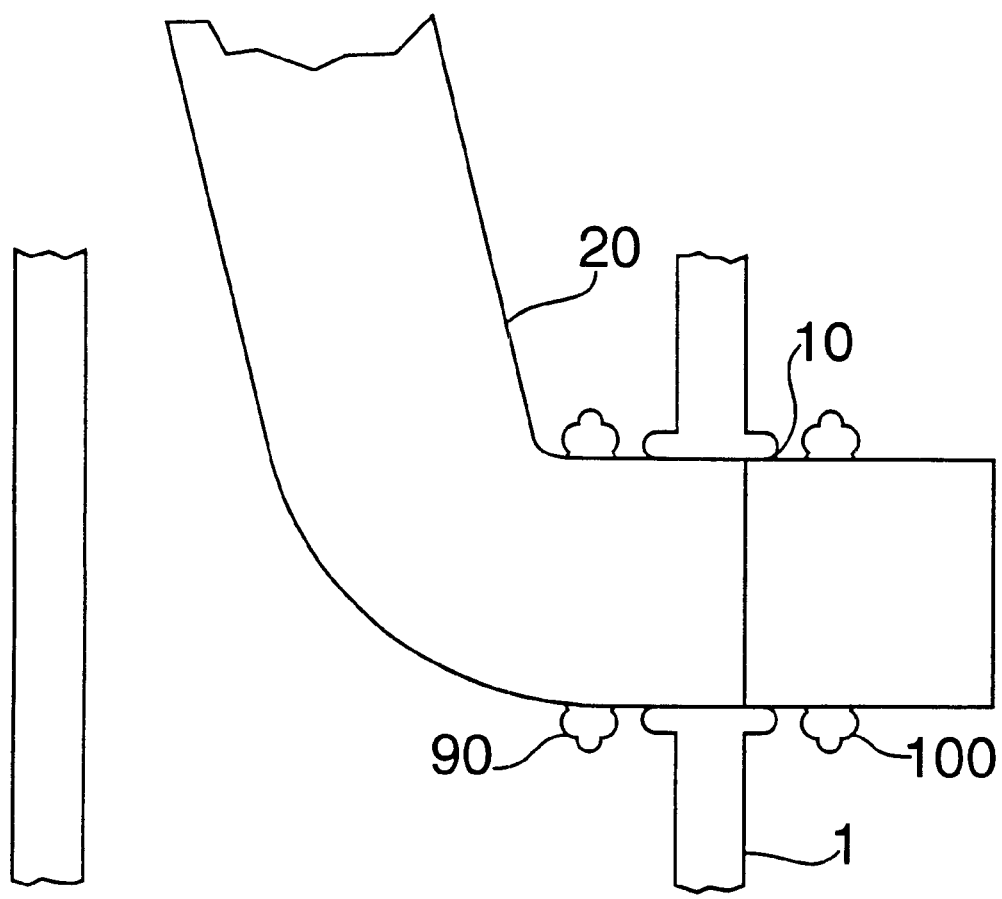
FIG. 8 is yet another view similar to FIG. 1a showing a delivery sheath which includes distal and proximal selectively enlargeable structures.

FIG. 8 shows delivery sheath 20 which includes proximal and distal selectively enlargeable structures 90, 100. Preferably, both selectively enlargeable structures 90, 100 are balloons which extend annularly around the exterior of delivery sheath 20 and project radially outward when inflated. Although the embodiment shown in FIG. 8 includes both proximal and distal selectively enlargeable structures, either one or both may be included. When enlarged, proximal selectively enlargeable structure 90 prevents more than the portion of delivery sheath 20 which is distal of the enlargeable structure from passing out of the tubular structure via the aperture. Similarly, when enlarged, distal selectively enlargeable structure 100 prevents the portion of delivery sheath 20 which is distal of the enlargeable structure from passing back in to the tubular structure via the aperture.

As an illustrative example of the application of the present invention, consider the following. Delivery sheath 20 (preferably about 4.0 mm in diameter) including cutting catheter 40 is introduced into organ structure 1 percutaneously through the femoral artery near the thigh. Cutting catheter 40 includes cutting head 45 (preferably about 3.5 mm in diameter). Delivery sheath 20 is positioned at access site 10, here the ascending aorta. Centering wire 30 is tracked through cutting catheter 40 and is caused to pierce the aortic artery at access site 10. Cutting catheter 40 is then tracked over centering wire 30 by either pushing or rotating (or a combination of both pushing and rotating) and caused to advance through the aortic wall. An approximately 3.5 mm aperture is created with tissue plug 60 retained in cutting head 45 and removed along with the cutting catheter 40. Delivery sheath 20 can now be advanced through the approximately 3.5 mm aperture created by the cutting catheter 40, causing organ structure 1 to stretch slightly (i.e., about 0.5 mm). This stretching is desirable because it provides a blood seal around delivery sheath 20 to prevent bleeding into the chest cavity. Delivery sheath 20 can now be used to introduce other catheters (including cameras, for example) from the femoral artery into the chest cavity for the purpose of diagnosis or intervention (e.g., grafts or TMR laser surgery).

To minimize patient trauma, delivery sheath 20, cutting catheter 40 and centering wire 30 are all preferably coupled to and controlled by a controller located on the outside of the patient.

Various methods and apparatus for delivering and installing plugs in walls of organ structures, as well as methods and apparatus for promoting the closing and healing of apertures in walls of organ structures, are available (e.g., of the type shown in Goldsteen et al. U.S. patent application Ser. No. 08/745,618, filed Nov. 7, 1996; Goldsteen et al. U.S. patent application Ser. No. 08/839,198, filed Apr. 23, 1997; and Sullivan et al. U.S. patent application Ser. No. 08/869,808, filed Jun. 5, 1997, all of which are hereby incorporated by reference herein).

Thus, it is seen that a method and apparatus for creating an aperture at an access site in a patient's existing tubular body organ structure and making it possible to access specific body cavities percutaneously, thereby minimizing patient trauma, is provided. One skilled in the art will appreciate that the present invention can be practiced by other than the described embodiments, which are presented for purposes of illustration and not of limitation, and the present invention is limited only by the claims which follow.

What is claimed is:

1. An apparatus for creating an aperture at an access site in a patient's existing tubular body organ structure comprising:
    a delivery sheath insertable axially along the interior of a portion of said existing tubular body organ structure from an insertion point which is remote from said access site to a location inside said tubular body organ structure adjacent said access site;
    a centering wire insertable axially along the interior of said delivery sheath from adjacent said insertion point and adapted for piercing through said patient's existing tubular body organ structure at said access site from inside said tubular body organ structure to outside said tubular body organ structure; and
    a cutting catheter insertable substantially coaxially over said centering wire and axially along the interior of said delivery sheath from adjacent said insertion point, said cutting catheter including a distal end adapted for advancing through said patient's existing tubular body organ structure at said access site by rotation of said cutting catheter to produce an annular cut through the tubular body organ structure from inside said tubular body organ structure to outside said tubular body organ structure to form said aperture by removal of tissue bounded by said annular cut.

2. The apparatus of claim 1 wherein said distal end of said delivery sheath includes a selectively enlargeable structure disposed on its exterior at a predetermined distance proximally from its distal end for selectively preventing the portion of said delivery sheath which is proximal of said enlargeable structure from passing out of said tubular structure via said aperture by selectively enlarging said selectively enlargeable structure.

3. The apparatus of claim 1 wherein said distal end of said delivery sheath includes a selectively enlargeable structure disposed on its exterior at a predetermined distance proximally from its distal end for selectively preventing the portion of said delivery sheath which is distal of said enlargeable structure from passing back into said tubular structure via said aperture by selectively enlarging said selectively enlargeable structure.

4. The apparatus of any one of claims 2 through 3 wherein said enlargeable structure comprises an inflatable balloon.

5. The apparatus of claim 1 wherein said distal end of said cutting catheter comprises a substantially circular cutting edge with an axially aligned recess for accepting a tissue plug generated during formation of said aperture.

6. The apparatus of claim 1 wherein said distal end of said cutting catheter comprises a substantially circular serrated cutting edge with an axially aligned recess for accepting a tissue plug generated during formation of said aperture.

7. The apparatus of claim 1 wherein a distal end portion of said centering wire is resiliently biased to deflect laterally after piercing through said tubular body organ structure.

8. The apparatus of claim 1 wherein a distal end portion of said centering wire includes struts mounted on said centering wire, said struts being resiliently biased to project from said center wire after the end portion of said centering wire pierces through from inside to outside of said patient's existing tubular body organ structure at said access site.

9. The apparatus of claim 8 wherein said struts comprise:
    a plurality of fingers spaced circumferentially around said centering wire, each of said fingers being resiliently biased to project from said centering wire.

10. The apparatus of claim 1 wherein a distal end portion of said centering wire includes a selectively enlargeable structure disposed on its exterior at a predetermined distance proximally from its distal end for selectively preventing the portion of said centering wire which is distal of said enlargeable structure from passing back into said tubular structure via said aperture by selectively enlarging said selectively enlargeable structure.

11. The apparatus of claim 10 wherein said enlargeable structure comprises an inflatable balloon.

12. The apparatus of claim 1 wherein said cutting catheter further includes a dilator positioned substantially coaxially over said cutting catheter.

13. An apparatus for creating an aperture at an access site in a patient's existing tubular body organ structure comprising:
    a delivery sheath insertable axially along the interior of a portion of said existing tubular body organ structure from an insertion point which is remote from said access site to a location inside said tubular body organ structure adjacent said access site;
    a centering wire insertable axially along the interior of said delivery sheath from adjacent said insertion point and adapted for piercing through said patient's existing tubular body organ structure at said access site from inside said tubular body organ structure to outside said tubular body organ structure; and
    a cutting catheter insertable substantially coaxially over said centering wire and axially along the interior of said delivery sheath from adjacent said insertion point, said cutting catheter including a distal end including a plurality of distally directed cutting edges, each of which is disposed in a respective one of a plurality of planes that extend radially out from said centering wire and that are spaced from one another around said centering wire, each of said cutting edges being inclined distally back from its end which is closest to the centering wire, for cutting through said patient's existing tubular body organ structure at said access site to form said aperture from inside said tubular body organ structure to outside said tubular body organ structure.

14. The apparatus of claim 13 wherein said distal end of said delivery sheath includes a selectively enlargeable structure disposed on its exterior at a predetermined distance proximally from its distal end for selectively preventing the portion of said delivery sheath which is proximal of said enlargeable structure from passing out of said tubular structure via said aperture by selectively enlarging said selectively enlargeable structure.

15. The apparatus of claim 14 wherein a distal end portion of said centering wire includes a selectively enlargeable structure disposed on its exterior at a predetermined distance proximally from its distal end for selectively preventing the portion of said centering wire which is distal of said enlargeable structure from passing back into said tubular structure via said aperture by selectively enlarging said selectively enlargeable structure.

16. The apparatus of claim 15 wherein said enlargeable structure comprises an inflatable balloon.

17. The apparatus of claim 14 wherein said cutting catheter further includes a dilator positioned substantially coaxially over said cutting catheter.

18. The apparatus of claim 13 wherein said distal end of said delivery sheath includes a selectively enlargeable structure disposed on its exterior at a predetermined distance proximally from its distal end for selectively preventing the portion of said delivery sheath which is distal of said enlargeable structure from passing back into said tubular structure via said aperture by selectively enlarging said selectively enlargeable structure.

19. The apparatus of any one of claims 14 through 15 wherein said enlargeable structure comprises an inflatable balloon.

20. The apparatus of claim 13 wherein a distal end portion of said centering wire is resiliently biased to deflect laterally after piercing through said tubular body organ structure.

21. The apparatus of claim 13 wherein a distal end portion of said centering wire includes struts mounted on said centering wire, said struts being resiliently biased to project from said centering wire after the end portion of said centering wire pierces through from inside to outside of said patient's existing tubular body organ structure at said access site.

22. The apparatus of claim 21 wherein said struts comprise:
a plurality of fingers spaced circumferentially around said centering wire, each of said fingers being resiliently biased to project from said centering wire.

23. A method for creating an aperture at an access site in a patient's existing tubular body organ structure comprising the steps of:
passing a delivery sheath axially along the interior of a portion of said existing tubular body organ structure from an insertion point which is remote from said access site to place a distal end of said delivery sheath inside said tubular body organ structure near said access site;
passing a centering wire axially along the interior of said delivery sheath from adjacent said insertion point;
piercing through from inside to outside of said patient's existing tubular body organ structure at said access site by causing a distal end portion of said centering wire to emerge from said distal end of said delivery sheath;
passing a cutting catheter substantially coaxially over said centering wire and axially along the interior of said delivery sheath from adjacent said insertion point;

forming said aperture by advancing a distal end of said cutting catheter through from inside to outside of said patient's existing tubular body organ structure at said access site by rotating said distal end to produce an annular cut through the tubular body organ structure, whereby tissue bounded by said annular cut is removed to produce said aperture; and
advancing said distal end of said delivery sheath through said aperture from inside to outside of said patient's existing tubular body organ structure, thereby dilating said patient's existing tubular body organ structure around said aperture and creating a fluid seal between said delivery sheath and said existing tubular body organ structure at said aperture.

24. A method for creating an aperture at an access site in a patient's existing tubular body organ structure comprising the steps of:
passing a delivery sheath axially along the interior of a portion of said existing tubular body organ structure from an insertion point which is remote from said access site to place a distal end of said delivery sheath inside said tubular body organ structure near said access site;
passing a centering wire axially along the interior of said delivery sheath from adjacent said insertion point;
piercing through from inside to outside of said patient's existing tubular body organ structure at said access site by causing a distal end portion of said centering wire to emerge from said distal end of said delivery sheath;
passing a cutting catheter substantially coaxially over said centering wire and axially along the interior of said delivery sheath from adjacent said insertion point, said cutting catheter including a distal end which comprises a plurality of distally directed cutting edges, each of which is disposed in a respective one of a plurality of planes that extend radially out from said centering wire and that are spaced from one another around said centering wire, each of said cutting edges being inclined distally back from its end which is closest to the centering wire;
forming said aperture by advancing said distal end of said cutting catheter through from inside to outside of said patient's existing tubular body organ structure at said access site so that the cutting edges produce a star-shaped array of cuts through the tubular body organ structure; and
advancing said distal end of said delivery sheath through said aperture from inside to outside of said patient's existing tubular body organ structure, thereby dilating said patient's existing tubular body organ structure around said aperture and creating a fluid seal between said delivery sheath and said existing tubular body organ structure at said aperture.

25. A method for creating an aperture at an access site in a patient's existing tubular body organ structure comprising the steps of:
placing a distal end of a delivery sheath near said access site;
passing a centering wire axially along the interior of said delivery sheath;
piercing through from out side to inside of said patient's existing tubular body organ structure at said access site by causing a distal end portion of said centering wire to emerge from said distal end of said delivery sheath;
passing a cutting catheter substantially coaxially over said centering wire and axially along the interior of said delivery sheath;

forming said aperture by advancing a distal end of said cutting catheter through from outside to inside of said patient's existing tubular body organ structure at said access site by rotating said distal end to produce an annular cut through the tubular body organ structure, whereby tissue bounded by said annular cut is removed to produce said aperture; and advancing said distal end of said delivery sheath through said aperture from outside to inside of said patient's existing tubular body organ structure, thereby dilating said patient's existing tubular body organ structure around said aperture and creating a fluid seal between said delivery sheath and said existing tubular body organ structure at said aperture.

26. A method for creating an aperture at an access site in a patient's existing tubular body organ structure comprising the steps of:

placing a distal end of a delivery sheath near said access site;

passing a centering wire axially along the interior of said delivery sheath;

piercing through from outside to inside of said patient's existing tubular body organ structure at said access site by causing a distal end portion of said centering wire to emerge from said distal end of said delivery sheath;

passing a cutting catheter substantially coaxially over said centering wire and axially along the interior of said delivery sheath, said cutting catheter including a distal end which comprises a plurality of distally directed cutting edges, each of which is disposed in a respective one of a plurality of planes that extend radially out from said centering wire and that are spaced from one another around said centering wire, each of said cutting edges being inclined distally back from its end which is closest to the centering wire;

forming said aperture by advancing a distal end of said cutting catheter through from outside to inside of said patient's existing tubular body organ structure at said access site so that the cutting edges produce a star-shaped array of cuts through the tubular body organ structure; and advancing said distal end of said delivery sheath through said aperture from outside to inside of said patient's existing tubular body organ structure, thereby dilating said patient's existing tubular body organ structure around said aperture and creating a fluid seal between said delivery sheath and said existing tubular body organ structure at said aperture.

* * * * *